(12) United States Patent
Lee et al.

(10) Patent No.: US 9,273,367 B2
(45) Date of Patent: Mar. 1, 2016

(54) OPTICALLY INDUCED CELL LYSIS BIOCHIP

(71) Applicant: National Cheng Kung University, Tainan (TW)

(72) Inventors: Gwo-Bin Lee, Tainan (TW); Yen-Heng Lin, Tainan (TW)

(73) Assignee: National Cheng Kung University, Tainan (TW)

( * ) Notice: Subject to any disclaimer, the term of this patent is extended or adjusted under 35 U.S.C. 154(b) by 80 days.

(21) Appl. No.: 14/451,502

(22) Filed: Aug. 5, 2014

(65) Prior Publication Data

US 2014/0342348 A1 Nov. 20, 2014

Related U.S. Application Data

(62) Division of application No. 12/585,327, filed on Sep. 11, 2009, now abandoned.

(30) Foreign Application Priority Data

Apr. 2, 2009 (TW) ................................ 98111068 A

(51) Int. Cl.
*C12Q 3/00* (2006.01)
*C12N 1/06* (2006.01)
*C12N 13/00* (2006.01)

(52) U.S. Cl.
CPC .. *C12Q 3/00* (2013.01); *C12N 1/06* (2013.01); *C12N 1/066* (2013.01); *C12N 13/00* (2013.01)

(58) Field of Classification Search
CPC ............. C12N 1/06; C12N 1/066; C12Q 3/00
See application file for complete search history.

(56) References Cited

U.S. PATENT DOCUMENTS

| 5,936,730 A | 8/1999 | Foley et al. |
| 6,429,417 B1 | 8/2002 | Street et al. |
| 7,015,031 B2 | 3/2006 | Cecchi et al. |

OTHER PUBLICATIONS

Valley et al., "In-Situ Single Cell Electroporation Using Optoelectronic Tweezers", Aug. 11-14 2008, Optical MEMS and Nanophotonics, 2008, IEEE/LEOS International Conference, pp. 74-75.
Valley et al., "Parallel single-cell light-induced electroporation and dielectrophoretic manipulation", Mar. 13, 2009, Lab Chip, 9, pp. 1714-1720.

*Primary Examiner* — Jonathan Hurst
(74) *Attorney, Agent, or Firm* — Bacon & Thomas, PLLC

(57) ABSTRACT

The present invention provides an optically induced cell lysis biochip, which comprises: an upper substrate made of a transparent, electrically conductive material; a lower substrate made of a transparent, electrically conductive material; a photoconductive layer formed under the lower surface of the upper substrate or on the upper surface of the lower substrate; and a chamber formed between the upper substrate and the lower substrate. When there is an electric potential difference between the upper and lower substrates, a light spot illuminated on the photoconductive layer can cause the impedance of the illuminated area to decrease, thereby causing the electric current to center on the illuminated area of the photoconductive layer. Further, the electric current flowing through the illuminated area can induce the cell lysis process of a target cell.

7 Claims, 6 Drawing Sheets

US 9,273,367 B2

OPTICALLY INDUCED CELL LYSIS BIOCHIP

CROSS REFERENCE TO RELATED APPLICATIONS

This application is a divisional application of U.S. patent application Ser. No. 12/585,327, filed on Sep. 11, 2009, now abandoned, which claims the benefit of Taiwan Application No. 98111068, filed on Apr. 2, 2009, the entire contents of which are incorporated herein by reference.

BACKGROUND OF THE INVENTION

1. Field of the Invention

The present invention relates to an optically induced cell lysis biochip, and more particularly, to a cell lysis method using a system which includes said biochip.

2. Description of the Related Art

In the biomedical field, researches focusing on a specific component within a single cell tend to become more and more sophisticated recently. Therefore, to extract the target proteins, nucleic acids or organelles from the tissues or cells of an organism has also been an important issue. However, traditional tools, including chemical, thermal, electric, ultrasonic, laser, and mechanical approaches, can only lyse a group of cells in a cell-containing solution and further obtain their cell components for study. If one intends to focus the study on the component of a specific cell, he needs to further separate within the group of cells using other methods so as to extract the target components, which is an exhausting and time-consuming process. Moreover, the cell components in the cell-containing solution, such as proteins and nucleus, would easily be denatured if the cell-containing solution is exposed under a non-physiological condition for a long time. Thus, traditional approaches as described above have prevented researchers from quickly extracting specific cell components, causing a research bottleneck in the biomedical field.

In view of the above, the present invention has been developed to provide a biochip and a system, with which a single cell can be lysed within a group of cells. Therefore, specific cell components can be further extracted for analysis with less time spent during the process.

SUMMARY OF THE INVENTION

For the purpose of extracting cell components more quickly for further analysis, the present invention provides a biochip and a system which can induce an electric field at a specific position under the illumination of a beam spot generating a transmembrane potential in the cell. With this approach, cell lysis can be performed using the optically induced electric field.

It is one aspect of the present invention to provide an optically induced cell lysis biochip, which comprises: an upper substrate made of a transparent, electrically conductive material; a lower substrate made of a transparent, electrically conductive material; a photoconductive layer formed under the lower surface of the upper substrate or on the upper surface of the lower substrate; and a chamber formed between the upper substrate and the lower substrate.

Preferably, the transparent, electrically conductive material is indium-tin-oxide (ITO).

Preferably, the photoconductive layer is made of an amorphous silicon material or a polymer material. The amorphous silicon material may be a material comprising cadmium sulfide (CdS), Se—As compound, or Se—Te compound. The polymer material may be poly(3-hexylthiophene) (P3HT) or [6,6]-phenyl C61-butyric acid methyl ester (PCBM).

It is another aspect of the present invention to provide a use of the biochip for cell lysis.

It is still another aspect of the present invention to provide an optically induced cell lysis system, which comprises: one said biochip; a power supply for providing an electric current for the upper substrate and the lower substrate of the biochip; a light source for generating a beam spot on the photoconductive layer; an image capture unit for capturing the interior image of the chamber of the biochip; a control unit for displaying the image captured by the image capture unit and for controlling the position and/or size of the illuminated area on the photoconductive layer illuminated by the light beam from the light source.

Preferably, the power supply provides an alternating electric current.

Preferably, the control unit is a computer.

It is yet another aspect of the present invention to provide a method of using the system for cell lysis, which comprises: (a) providing the system; (b) loading a cell-containing solution in the chamber of the biochip of the system; (c) capturing the image of inside of the chamber of the biochip by the image capture unit to confirm the location and size of the target cells; and (d) using said control unit to control said light source for the position and/or size of the illuminated area on the photoconductive layer, thereby inducing the electric current to center on the illuminated area of the photoconductive layer to flow therethrough.

BRIEF DESCRIPTION OF THE DRAWINGS

The above objects and advantages of the present invention will become more readily apparent to those ordinarily skilled in the art after reviewing the following detailed descriptions and accompanying drawings, in which.

DETAILED DESCRIPTION OF THE PREFERRED EMBODIMENTS

Figure 1:
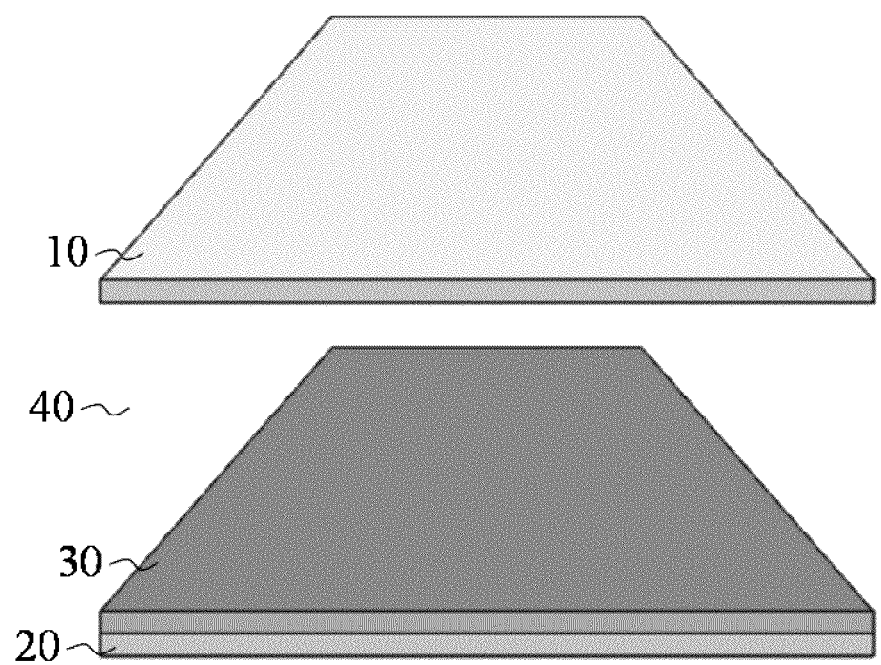
FIG. 1 is a schematic illustration that shows the structure of an optically induced cell lysis biochip of the present invention.

FIG. 1 is a schematic illustration that shows the structure of an optically induced cell lysis biochip 100 of the present invention. The cell lysis biochip 100 comprises: an upper substrate 10, a lower substrate 20, a photoconductive layer 30, and a chamber 40. The upper substrate 10 and the lower substrate 20 are made of a transparent, electrically conductive material. Thus, light is allowed to transmit through the material, and an image capture unit can capture what occurs inside the chamber; the material is also electrically conductive so as to allow electric currents to flow through. The material of the substrates may include, but is not limited to, indium-tin-oxide (ITO).

The photoconductive layer 30 of the cell lysis biochip 100 may be formed under the lower surface of the upper substrate 10 or on the upper surface of the lower substrate 20 (the illustrated embodiment in FIG. 1 only shows the latter). When a light beam transmits through the upper substrate 10 or lower substrate 20 and a beam spot is illuminated on the photoconductive layer 30, the impedance of the illuminated area is decreased. For example, if an amorphous silicon layer is used as the photoconductive layer 30, the impedance can be decreased by 4-5 orders of magnitude. Then, the electric current bias drops across the photoconductive layer 30 around the illuminated area. This induces a trans-membrane potential across the cell membrane and the cell would be lysed. It may be easily understood that the material of the photoconductive layer 30 shall have a feature of decreased impedance with light illumination. Therefore, said material may include, but is not limited to, an amorphous silicon material or a polymer material. The amorphous silicon material may include, but is not limited to, cadmium sulfide (CdS), Se—As compound, or Se—Te compound; the polymer material may include, but is not limited to, poly(3-hexylthiophene) (P3HT) or [6,6]-phenyl C61-butyric acid methyl ester (PCBM).

The chamber 40, which is formed between the upper substrate 10 and the lower substrate 20, may be a chamber with an opening. The opening serves as the entry for loading or unloading the cells to be lysed. Alternatively, the chamber 40 may be an enclosed chamber, wherein the cells to be lysed are introduced into/drawn from the chamber from/to a sampling means.

Figure 2A:
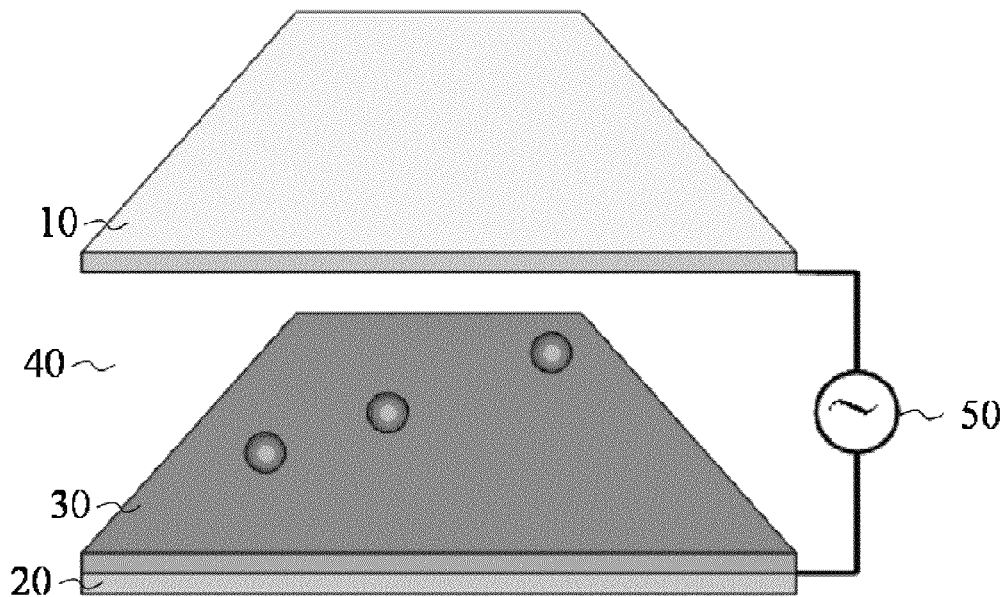
FIG. 2A is a schematic illustration that shows loading the cells for lysis into the optically induced cell lysis biochip of the present invention.
Figure 2B:
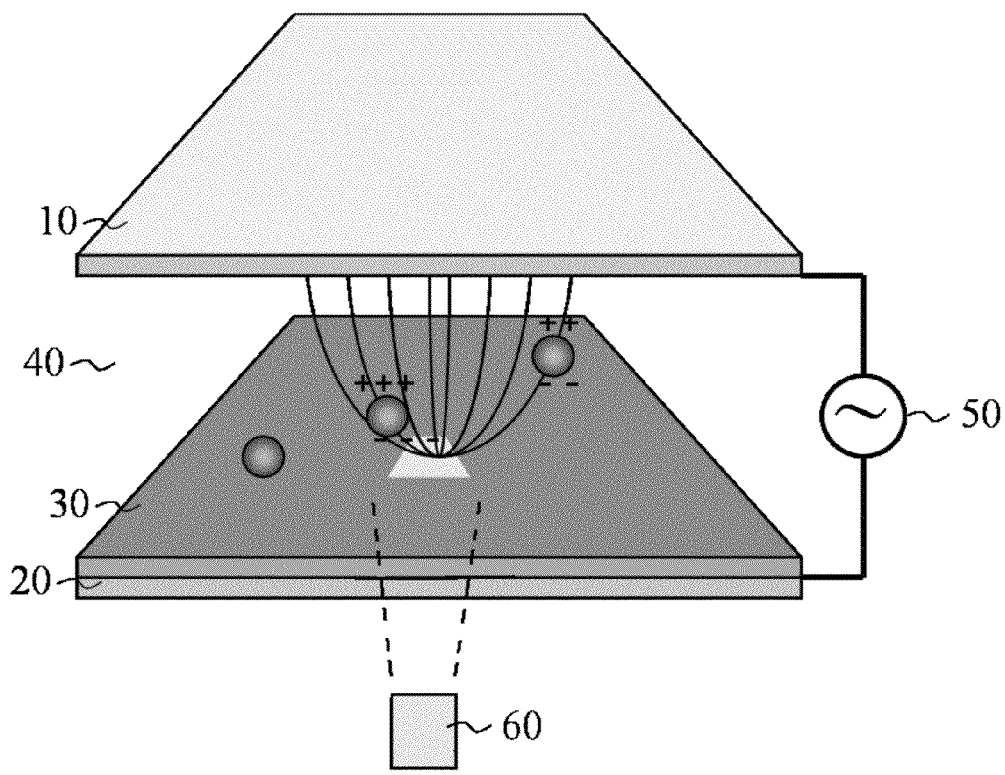
FIG. 2B is a schematic illustration that shows the optically induced cell lysis biochip of the present invention when it is supplied with power and illuminated with a light beam.

The operating principle for cell lysis using the biochip of the present invention is shown in FIGS. 2A and 2B. Referring to FIG. 2A, before a light beam is projected onto the photoconductive layer 30, a power supply 50 generates an electric potential difference between the upper substrate 10 and the lower substrate 20. Since the impedance of the photoconductive layer 30 is still high now, the electric current does not induce cell lysis for the cells in the chamber 40.

Referring to FIG. 2B, a light source 60 is used to project a beam spot onto the photoconductive layer 30 first. Then, since the impedance of the photoconductive layer 30 has decreased after the layer is illuminated, a transmembrane potential is induced across the cell sandwiched between the upper substrate 10 and the lower substrate 20. As a result, the cell in the illuminated area can be lysed.

Figure 3:
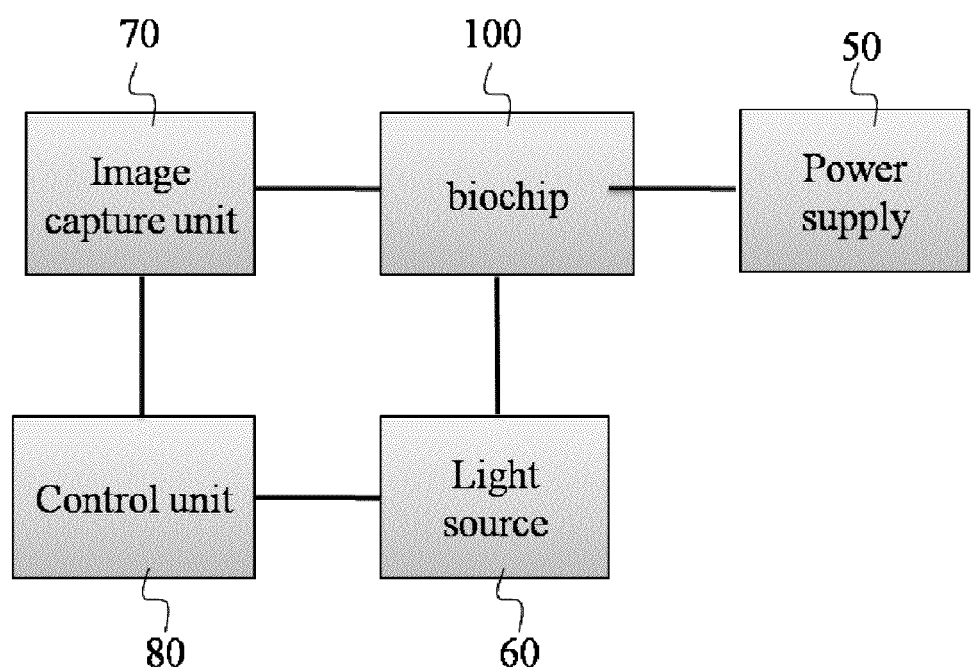
FIG. 3 is a block diagram that shows an optically induced cell lysis system of the present invention.

It may be easily understood that, as shown in FIG. 3, other than the cell lysis biochip 100, an optically induced cell lysis system of the present invention further comprises a power supply 50, a light source 60, an image capture unit 70 and a control unit 80. The power supply 50 is used to generate an electric potential difference between the upper substrate 10 and the lower substrate 20 of the cell lysis biochip 100, so that a transmembrane electric potential difference for the cell in the chamber 40 is induced. The power supply is not limited to certain types; however, a power supply that uses alternating current (AC) power would generate higher voltage and is preferred.

The light source 60 is used to produce a light beam projected on the photoconductive layer 30 of the cell lysis biochip 100 so as to cause the impedance of the photoconductive layer to decrease. The angle between the light beam and the photoconductive layer may depend on the needs of the cell lysis process. The light source 60 may produce a light beam that is perpendicular to the photoconductive layer or that forms an angle between 0°~90° with it, as long as the light beam is able to cause the impedance of the photoconductive layer to decrease and induce a transmembrane potential of the cells in the illuminated area. The light source 60 may include, but is not limited to, a micro projector.

The image capture unit 70 is used to capture the interior image of the cell lysis biochip 100. The captured images may be dynamic or static, and may be displayed on a display device through any known means. For example, when the control unit 80 is a computer, the captured images may be displayed on its monitor. Preferably, the images captured by the system of the present invention are real-time images, and also, they can be enlarged to a scale that is visible to the naked eye. The image capture unit 70 may include, but is not limited to, a microscope.

The control unit 80 is connected to the light source 60 to control it for adjusting the position and size of the illuminated area on the photoconductive layer 30, which is illuminated by the light beam generated from the source 60. Therefore, the cells in the illuminated area can be lysed because of the induced transmembrane potential. The control unit 80 may also be connected to the image capture unit 70, so that the interior images of the chamber can be directly sent to the control unit 80, making it easier to control the light source 60 for adjusting the position and size of the illuminated area. The control unit 80 may include, but is not limited to, a computer.

From the above description, it is easily understood that a method of using the optically induced cell lysis system of the present invention includes the steps of: (a) providing an optically induced cell lysis system; (b) loading a cell-containing solution into the chamber of the biochip of the system; (c) capturing the interior image of the chamber of the biochip by the image capture unit to confirm the position and size of a target cell; and (d) using the control unit to control the light source to project a beam spot onto the photoconductive layer, wherein the position/size of the beam spot corresponds that of the target cell.

Example 1

Figure 4:
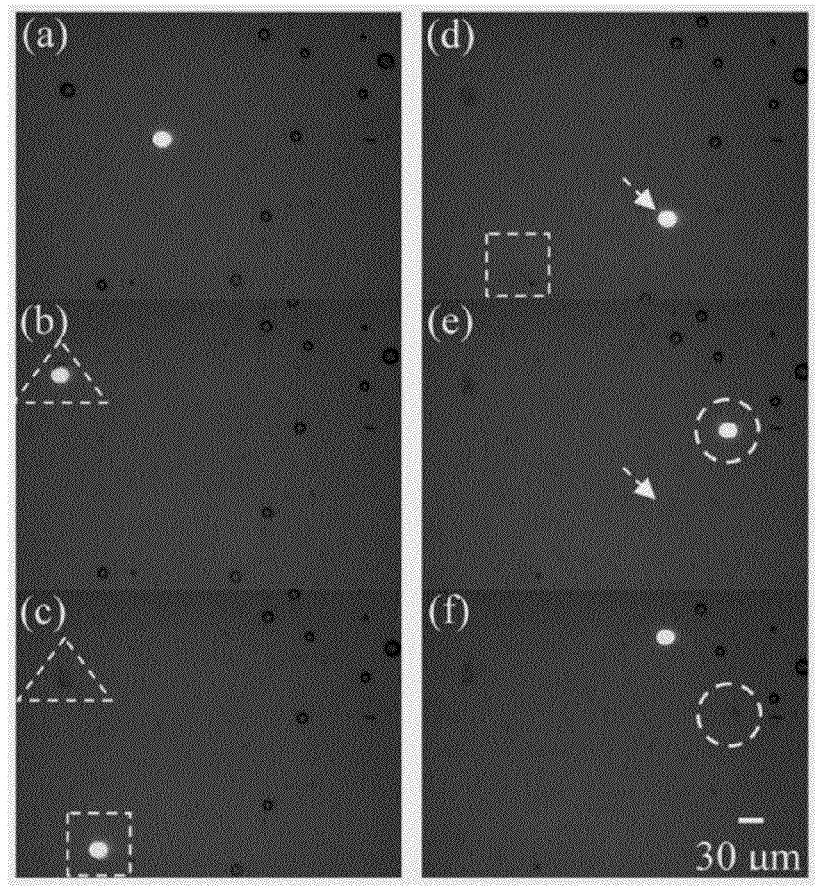
FIG. 4 shows a series of images of lysing the cells individually and sequentially using the optically induced cell lysis system of the present invention.

Lysing Cells Individually and Sequentially with the Optically Induced Cell Lysis System FIG. 4 shows a series of photographs of lysing the cells individually and sequentially using the optically induced cell lysis system of the present invention. In this embodiment, a solution containing fibroblast cells (average size=16 µm) and oral cancer cells (average size=14 µm) is prepared first, made isotonic to a sucrose solution (about 0.2M). The cell-containing solution is then introduced into the optically induced cell lysis biochip of the present invention, thereby sandwiching the cells for lysis between the two ITO glass plates. After the solution becomes stable, an alternating current (at 20 kHz, 7V p.p.) is supplied between the two ITO glass plates. Also, a computer is used to control a commercial projector, used as a light source, to project a beam spot (with an illuminating power density of 117 nW/µm$^2$) onto the photoconductive layer placed on the lower ITO glass plate. A specific cell on the photoconductive layer can thus be lysed. Images shown in FIG. 4 are at 50× magnification. FIG. 4(a) shows a cell that is to be lysed; the cell is illuminated by a beam spot projected from the light source. Each fibroblast cell marked by the dotted triangle, square, and circle shown in FIGS. 4(b), 4(c), and 4(e) respectively are the cells to be lysed, with each cell illuminated by a beam spot. Then, because the beam spot has induced the cell lysis process for each cell, only the cell debris is left in each dotted symbol shown in FIGS. 4(*c*), 4(*d*), and 4(*f*).

Example 2

Figure 5:
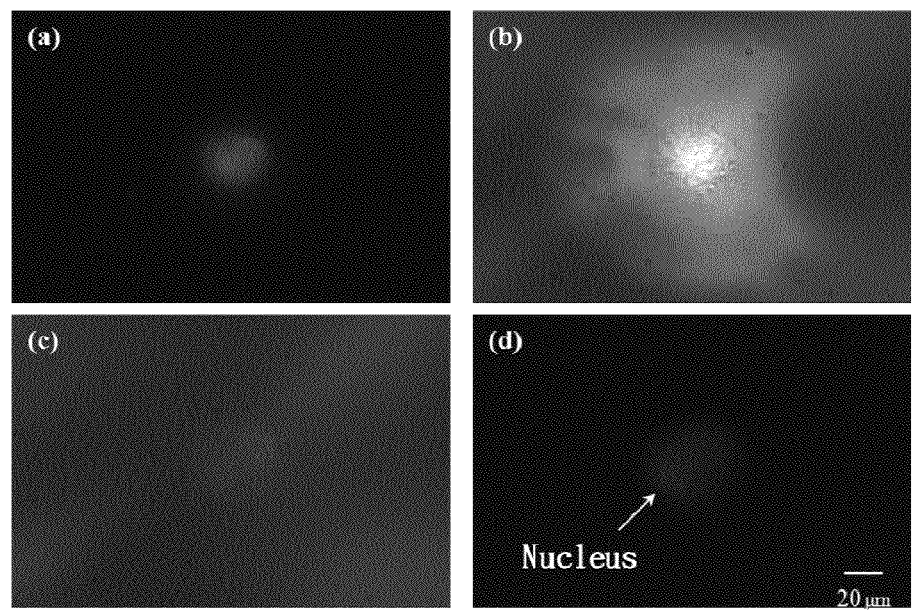
FIG. 5 shows a series of images of selectively disrupting the cell membrane of a specific cell without damaging its nucleus using the optically induced cell lysis system of the present invention.

Selectively Disrupting the Cell Membrane of a Specific Cell without Damaging its Nucleus The photographs in FIG. 5 show the process of selectively disrupting the cell membrane of a specific cell obtained from the solution containing fibroblast cells. In this embodiment, a solution containing fibroblast cells is prepared first, made isotonic to a sucrose solution (about 0.2M). Next, a fluorescent dye kit (LIVE/DEAD® Viability/Cytotoxicity Kit L-3224, Molecular Probes, USA) including two dye colors is used to stain the cells while confirming their membrane remains intact. The green dye is retained within a viable cell membrane, thus producing a green fluorescence when the membrane remains intact. The red dye is transmitted through the damaged membrane and then stains the nucleus, thus producing a red fluorescence when the cell membrane is ruptured while the nucleus remains intact. In this embodiment, a cell-containing solution that has been stained is introduced into the optically induced cell lysis biochip of the present invention first. After the solution becomes stable, an alternating current (at 20 kHz, 7V p.p.) is supplied between the two ITO glass plates, and a computer is used to control the light source to project a beam spot (with an illuminating power density of 73 nW/$\mu m^2$) on a specific cell for lysis. FIG. 5 shows the lysis process of a single fibroblast cell, wherein FIG. 5(*a*) shows the fibroblast cell with green fluorescence. When a light beam is projected onto the cell, the cell is slightly swollen as shown in FIG. 5(*b*). In FIG. 5(*c*), when the light source is shut, it is observed that the cell membrane has been ruptured. And as indicated by the arrow shown in FIG. 5(*d*), the nucleus is stained with red fluorescence, meaning the nucleus of the cell remains intact while its membrane has been ruptured. This is because the induced electric field produces a transmembrane potential that can only rupture the cell membrane, and thus, the nucleus is not damaged. The magnitude of the provided electric field depends on the size of a cell.

Example 3

Figure 6:
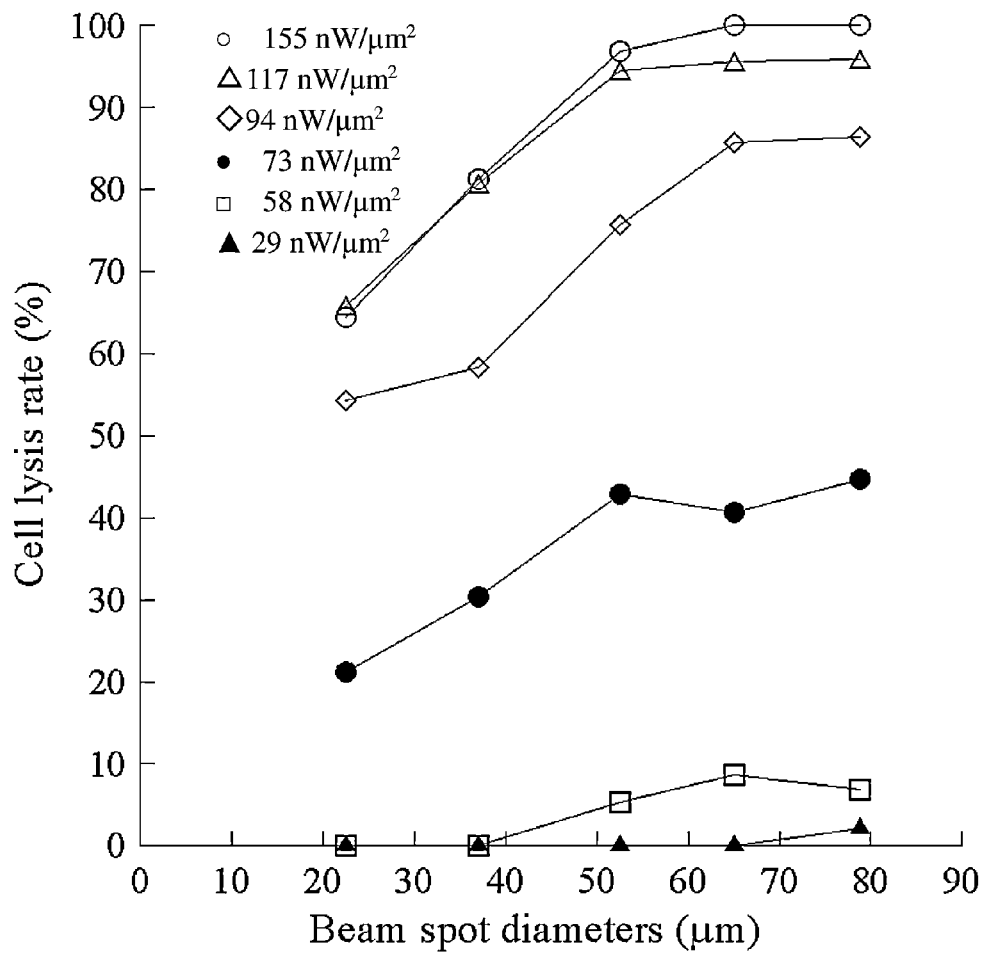
FIG. 6 is a chart showing the relationship between the cell lysis rate and the spot diameter of the illumination light at various illumination power densities using the optically induced cell lysis system of the present invention.

Relationship Between Cell Lysis Rate and Spot Diameter/Power Density of the Illumination Light Two major parameters, including the size of light spot and the illumination power density, may affect the cell lysis rate of the optically induced cell lysis biochip according to the present invention. Referring to FIG. 6, in this embodiment, a cell-containing solution isotonic to a sucrose solution (about 0.2M) is introduced into the biochip of the present invention and supplied with an alternating current as well as illumination light. The illumination light is provided at various illumination power densities (155, 117, 94, 73, 58, and 29 nW/$\mu m^2$, respectively) and with different illumination spot diameters (22.5, 37.0, 52.5, 65.0, and 78.8 $\mu m$, respectively). The cell lysis rates in different conditions are observed, as shown in the chart of FIG. 6. With the light spot diameter fixed at 78.8 $\mu m$, the cell lysis rate is 100% when a high illumination power density, such as 155 nW/$\mu m^2$, is provided, and the lysis rate becomes 2.13% when a low illumination power density, such as 29 nW/$\mu m^2$, is provided. It is thus observed that with the same light spot diameter, the higher the illumination power density, the higher the cell lysis rate.

In summary, lysing a specific cell or rupturing only the membrane of a single cell is allowed using the cell lysis system of the present invention. Therefore, extracting a specific cytoplasm, organelle, or nucleus component of a single cell for further analysis is facilitated. Also, denaturations of substances, such as protein or nucleic acid, during the lysis process can be eliminated. And less operation time is consumed due to fewer process steps, minimizing human errors and the amount of the samples being used. In addition, the biochip of the present invention is advantageous in that it allows a sample that has been lysed to be analysed once again; as a result, different cells of a single tissue or different organelles of a single cell can be analyzed.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims, which are to be accorded with the broadest interpretation so as to encompass all such modifications and similar structures. Therefore, the above description and illustration should not be taken as limiting the scope of the present invention which is defined by the appended claims.

What is claimed is:

1. A method of using a system for cell lysis, which comprises:
   (a) providing an optically induced cell lysis system, which comprises:
      an optically induced cell lysis biochip, which comprises:
         an upper substrate made of a transparent, electrically conductive material;
         a lower substrate made of a transparent, electrically conductive material;
         a photoconductive layer formed under the lower surface of said upper substrate or on the upper surface of said lower substrate; and
         a chamber formed between said upper substrate and said lower substrate;
      a power supply for providing an electric current for the upper substrate and the lower substrate of said biochip;
      a light source for generating a beam spot on said photoconductive layer;
      an image capture unit for capturing an interior image of the chamber of said biochip;
      a control unit for displaying the image captured by said image capture unit and for controlling the position and/or size of the illuminated area on said photoconductive layer illuminated by said light beam from said light source;
   (b) loading a cell-containing solution into the chamber of said biochip of the system;
   (c) capturing the interior image of the chamber of said biochip by the image capture unit to confirm the location and size of a target cell; and
   (d) using said control unit to control said light source for the position and/or size of the illuminated area on the photoconductive layer, thereby inducing the electric current to center on the illuminated area of the photoconductive layer to flow therethrough, wherein the light source provides an illumination light having an illumination power density of at least 29 nW/$\mu m^2$ and an illumination spot diameter of at least 22.5 $\mu m$.

2. The method of claim 1, wherein the transparent, electrically conductive material is indium-tin-oxide (ITO).

3. The method of claim 1, wherein said photoconductive layer is made of an amorphous silicon material or a polymer material.

4. The method of claim 3, wherein said amorphous silicon material comprises cadmium sulfide (CdS), Se—As compound or Se—Te compound.

5. The method of claim 3, wherein said polymer material is poly(3-hexylthiophene) (P3HT) or [6,6]-phenyl C61-butyric acid methyl ester (PCBM).

6. The method of claim 1, wherein said power supply provides an alternating electric current.

7. The method of claim 1, wherein said control unit is a computer.

* * * * *